(12) United States Patent
Wang

(10) Patent No.: US 7,759,309 B2
(45) Date of Patent: Jul. 20, 2010

(54) USE OF POLYPEPTIDES IN TREATING TISSUE INJURY

(75) Inventor: Yanming Frank Wang, Beverly, MA (US)

(73) Assignee: Yanming Wang, Malden, MA (US)

( * ) Notice: Subject to any disclaimer, the term of this patent is extended or adjusted under 35 U.S.C. 154(b) by 8 days.

(21) Appl. No.: 11/751,273

(22) Filed: May 21, 2007

(65) Prior Publication Data

US 2007/0275896 A1 Nov. 29, 2007

Related U.S. Application Data

(60) Provisional application No. 60/802,082, filed on May 19, 2006.

(51) Int. Cl.
*A61K 38/38* (2006.01)
*C07K 14/00* (2006.01)
*A61K 38/01* (2006.01)

(52) U.S. Cl. ............................ 514/12; 514/2; 530/350; 424/9.1

(58) Field of Classification Search ...................... 514/2, 514/12; 530/350; 424/9.1
See application file for complete search history.

(56) References Cited

U.S. PATENT DOCUMENTS

| | | | |
|---|---|---|---|
| 4,446,154 | A | 5/1984 | Osterholm |
| 5,407,428 | A | 4/1995 | Segall |
| 6,500,809 | B1 | 12/2002 | Frazer |
| 7,387,798 | B2 | 6/2008 | Wang |
| 2004/0138125 | A1 | 7/2004 | Wang |
| 2004/0142906 | A1 | 7/2004 | Wang |
| 2006/0034946 | A1 | 2/2006 | Wang |
| 2006/0057065 | A1 | 3/2006 | Wang |
| 2006/0057067 | A1 | 3/2006 | Wang |
| 2006/0073098 | A1 | 4/2006 | Wang |
| 2006/0128797 | A1 | 6/2006 | Wang |
| 2006/0128798 | A1 | 6/2006 | Wang |

FOREIGN PATENT DOCUMENTS

CN 1160721 * 10/1997

OTHER PUBLICATIONS

Lin et al., CN1160721, English Abstract, (1997).*
Blsera J et al. An "Oncometer" for clinical measurement of colloid osmotic pressure of plasma. Clinical Chemistry. 1978 24:1586-1589.
Zinderman CE, Landow L, Wise R P. Anaphylactoid reactions to Dextran 40 and 70: reports to the United States Food and Drug Administration, 1969 to 2004. J. Vasc. Surg. 2006 43:1004-1009.
Fishman RA. Exchange of albumin between plasma and cerebrospinal fluid. Am. J. Physiol. 1953. 175:96-98.
Griffin D E, Giffels J. Study of protein characteristics that influence entry into the cerebrospinal fluid of normal mice and mice with encephalitis. J. Clin. Invest. 1982. 70:289-295.
Kumagai AK, Eisenberg J B, Paradridge W M. Absorptive mediated endocytosis of cationized albumin and .beta.-endorphin-cationized albumin chimeric peptide by isolated brain capillaries. J. Biol. Chem. 1987. 262:15214-15219.
Lu W, Zhang Y, Tan Y Z, Hu K L, Jiang X G, Fu S K. Cationic albumin-conjugated pegylated monoparticles as novel drug carrier for brain delivery. Journal of controlled release. 2005. 107:428-448.
Pardridge W M, Kumagai A K, Eisenberg J B. Chimeric peptides as a vehicle for peptide pharmaceutical delivery through the blood-brain barrier. Biochem Biophys Res Commun. Jul. 15, 1987; 146(1):307-13.
Pardridge W M, Triguero D, Buciak J L. Beta.-Endorphin chimeric peptides: Transport through the Blood-brain barrier in vivo and cleavage of disulfide linkage by brain. Endocrinology. 1990/ 126:977-984.
Pardridge W M, Triguero D, Nuciak J, Yang J. Evaluation of cationized rat albumin as potential blood-brain barrier drug transport vector. The Journal of pharmacology and experimental therapeutics. 1990. 255: 893-899.
Pardridge W M. Drug delivery to the brain. J Cereb Blood Flow Metab. 1997 17:713-731.
Sakane T, Pardridge W M. Carboxyl-directed pegylation of brain-derived neurotrophic factor markedly reduces systemic clearance with minimal loss of biologic activity. Pharmaceutical Research. 1997. 14:1085-1091.
Wu D, Pardridge W M. Neuroprotection with noninvasive neurotrophin delivery to the brain. Proc. Natl. Acad. Sci. USA. 1999. 96:254-259.
Zhang Y, Pardridge W M. Conjugation of brain-derived neurotrophic factor to a blood-brain barrier drug targeting system enables neuroprotection in regional brain ischemia following intravenous injection of the neurotrophin. Brain Research. 2001. 889:49-56.
Zhang Y, Pardridge W M. Neuroprotection in transient focal brain ischemia after delayed intravenous administration of brain-derived neurotrophic factor conjugated to a blood-brain barrier drug targeting system. Stroke. 2001. 32:1378-1384.
Pardridge W M. Targeting neurotherapeutic agents through the blood-brain barrier. Arch. Neurol. 2002. 59:35-40.
Pardridge W M. Strategies for drug delivery through the blood brain barrier. Neurobiology of aging. 1989. 10:636-637.
Song B W, Vinters H V, Wu D, Pardridge W M. Enhanced neuroprotective effects of basic fibroblast growth factor in regional brain ischemia after conjugation to a blood brain barrier delivery vector. J. Pharmacol. Exp. Ther. 2002. 301:605-610.
Hoare D G, Koshland D E. A method for the quantitative modification and estimation of carboxylic acid groups in proteins. J. Biol. Chem. 1967 242:2447-2453.
Johansson BB. New concepts of a blood-brain Barrier. The role the endothelial cell surface charge for blood-brain barrier function. Plenum Press New York. 1995.

(Continued)

Primary Examiner—Chih-Min Kam

(57) ABSTRACT

This disclosure relates to methods for treating tissue injury in a mammal. The methods include administering a therapeutically effective amount of a polypeptide having an isoelectric point of at least about 4.8 and/or a molecular weight of less than about 30 kDa to the mammal.

2 Claims, No Drawings

OTHER PUBLICATIONS

Pardridge W M, Kang Y S, Diagne A, Zack J A. Cationized hyperimmune immunoglobulins: pharmacokinetics, toxicity evaluation and treatment of human immunodeficiency virus-infected human-peripheral blood lymphocytes-severe combined immune deficiency mice. J. Pharmacol. Exp. Ther. Jan. 1996; 276(1):246-252.

Shimon-Hophy M. Wadhwani K C. Chandrasekaran K, Larson D., Smith Q R. Rapoport S I. Regional blood-brain barrier transport of cationized bovine serum albumin in awake rats. Am. J. Physiol. 1991. 261:R478-483.

Wadhwani K C. Shimon-Hophy M. Rapoport S I. Enhanced permeabilities of cationized-bovine serum albumins at the blood nerve and blood-brain barrier in awake rats. J. Neurosci. Res. 1992. 32:407-414.

Pardridge W M. Neuroprotection in stroke: is it time to consider large-molecule drugs? Drug Discovery Today. 2001. 6:751-753.

Pardridge W M. Molecular Trojan horses for blood-brain barrier drug delivery. Curr. Opin. Pharmacol. Oct. 2006; 6(5):494-500.

Wang YF, Gwathmey JK, Zhang G, Soriano SG, He S, Wang Y. Cerebrospinal fluid may mediate CNS ischemic injury. Cerebrospinal Fluid Research. 2005 2:7.

Salmon JB, Mythen MG. Pharmacology and physiology of Colloids. Blood Reviews. 1993. 7: 114-120.

Barron ME, Wilkes MM, Navickis RJ. A systematic review of the comparative safety of colloids. Arch Surg 2004. 139: 552-563.

Vincent JL, et al. Morgidity in hospitalized patients receiving human albumin: A meta analysis of randomized, controlled trials. Crit Care med. 2004 32:2029_2038.

Belayev L et al. Human albumin therapy of acute ischemic stroke. Stroke 2001 32:553-560.

Lisa D et al. Serum albumin improves recovery from spinal cord injury *Journal of Neuroscience Research*. 2007 85:1558-1567.

Horstick G et al. Early albumin infusion improves global and local hemodynamics and reduces inflammatory response in hemorrhagic shock. *Crit Care Med.* 2002 30:851-855.

Powers KA et al. Twenty-five percent albumin prevents lung injury following shock/resuscitation. *Crit Care Med.* 2003 31:2355-2363.

Ginsberg MD et al. Diminution of metabolism/blood flow uncoupling following traumatic brain injury in rats in response to high-dose human albumin treatment. *J Neurosurg* 2001 94:499-509.

Watts JA, Maiorano PC. Trace amounts of albumin protect against ischemia and reperfusion injury in isolated rat hearts. *J Mol Cell Cardiol.* 1999 31:1653-1662.

Arroyo V. Review article: albumin in the treatment of liver diseases—new features of a classical treatment. *Alimentary Pharmacology & Therapeutics*. 2002 16: suppl 5:1-5.

Sort P et al. Effect of intravenous albumin on renal impairment and mortality in patients with cirrhosis and spontaneous bacterial peritonitis. *N Engl J Med*. 1999, 341:403-409.

Ikezawa F et al. Albumin infusion after reperfusion prevents gut ischemia-reperfusion induced gut-associated lymphoid tissue atrophy. *Journal of Parenteral and Enteral Nutrition*. 2006 30: 380-387.

Guyton AC. Hall JE. Textbook of Medical Physiology, ninth edition, Chapter 16. p. 183-197 WB Saunders company, (1995).

Guyton AC. Hall JE. Textbook of Medical Physiology, ninth edition, Chapter 25. p. 297-313 WB Saunders company, (1995).

Ames A, Wright RL, Kowada M, Thurston JM, Majno G. Cerebral ischemia: II. The no-reflow phenomenon. Am. J. Pathol. 1968; 52(2):437-453.

Kloner R A. Foreword-No-reflow: Basic science to a clinical phenomenon. Basic Res Cardiol. 2006. 101:357-358.

Fischer M, Hossmann K A. No-reflow after cardiac arrest. Intensive Care Med. 1995; 21(2):132-41.

Bottiger B W, Krumnikl J J, Gass P, Schmitz B, Motsch J, Martin E. The cerebral "no-reflow" phenomenon after cardiac arrest in rats. Influence of low-flow reperfusion. Resuscitation. 1997; 34(1):79-87.

Follis F, Miller K, Seremin O U, Pett S, Kessler R, Temes T, Wernly J A. Experimental delayed postischemic spinal cord hypoperfusion after aortic cross-clamping. Can. J. Neurol Sci. 22 (1995) 202-207.

Milhorat TH, Hammock MK, Fenstermacher JD, Levin VA. Cerebrospinal fluid production by the choroids plexus and brain. Science 1971; 173: 330-332.

Milhorat T H: choroids plexus and cerebrospinal fluid production. Science 1969, 166:1514-1516.

Rosenberg G A, Kyner W T, Estrada E. Bulk flow of brain interstitial fluid under normal and hyperosmolar conditions. Am J Physiol. 1980. 238:F42-49.

Abbott N J. Evidence for bulk flow of brain interstitial fluid: significance for physiology and pathology. Neurochemistry International. 2004; 45:545-5452.

Watkins S, Madison J, Galliano M, Minchiotti L, Putnam F W. Analbuminemia: three cases resulting from different point mutations in the albumin gene. Proc. Natl. Acad: Sci. USA. 1994. 91:9417-9421.

Ruffner D E. Dugaiczyk A. Splicing mutation in human hereditary analbuminemia. Proc. Natl. Acad. Sci. USA. 1988. 85:2125-2129.

Nagase S. Shimamune K. Albumin-deficient rat mutant. Science. 1979. 205:590-591.

Hua L. et al. Elevation of serum albumin levels in nagase analbuminemic rats by allogeneic bone marrow cell transplantation. Eur. Surg. Res. 2005. 37:111-114.

Fluid physiology. 7.3 Colloids. http://www.anaesthesiamcq.com/FluidBook/fl7-3.php.

Fluid physiology. 2.4 Colloid osmotic pressure. http://www.anaesthesiamcq.com/FluidBook/fl2_4.php.

Trüeb B, Winterhalter KH. Type VI collagen is composed of a 200 kd subunit and two 140 kd subunits. The EMBO Journal 1986 5:2815-2819.

Watts JA, Maiorano PC. Trace amounts of albumin protect against ischemia and reperfusion injury in isolated rat hearts. J Mol Cell Cardiol 1999 31:1653-1662.

Rohatgi T, Sedehizade F, Reymann KG, Reiser G. Protease-activated receptors in neuronal development, Neurodegeneration, and neuroprotection: Thrombin as signaling molecule in the brain. The Neuroscientist. 2004 10:501-512.

Striggow F et al. The protease thrombin is an endogenous mediator of hippocampal neuroprotection against ischemia at low concentrations but causes degeneration at high concentrations. Proc. Natl. Acad. Sci. USA. 2000. 97:2264-2269.

Altman GH et al. Silk-based biomaterials. Biomaterials. 2003 24: 401-416.

Benn SC et al. Hsp27 upregulation and phosphorylation is required for injured sensory and motor neuron survival. Neuron. 2002 36:45-56.

Liu Y, et al. Neuroprotective effect of treatment with human albumin in permanent focal cerebral ischemia: histopathology and cortical perfusion studies. European Journal of pharmacology. 2001 428:193-201.

Granger DN et al. Physiologic basis for the clinical use of albumin solutions. Surgery, Gynecology and Obstetrics. 1978 146:97-104.

Guyton AC. Hall JE. Textbook of Medical Physiology, ninth edition, Chapter 2. p. 23 WB Saunders company, (1995).

Bull HB, Breese K. Binding of water and electrolytes to proteins. An equilibrium dialysis study. Biopolymers. 1976 15:1573-1583.

Kuntz ID, Kauzmann W. Hydration of proteins and polypeptides. Adv Proteins and Polypeptides. 1974 28:239-345.

Cochrance injuries group albumin reviewers. Human albumin administration in critically ill patients: systematic review of randomized controlled trials. BMJ. 1998 317:235-40.

Unger JK et al. Albumin and hydroxyethyl starch 130 kDa/0.4 improve filter clearance and haemocompatibility in haemo- and plasmafiltration—an in vitro study. Nephrol Dial Transplant. 2005 20:1922-1931.

Napolitano L. Resuscitation following trauma and hemorrhagic shock: Is hydroxyethyl starch safe? Critical Care Medicine. 1995 23: 795-797.

Anaphylactoid reactions to Dextran 40 and 70: Reprots to the united states food and drug administration, 1969-2004. J Vasc Surg. 2006 43:1004-1009.

* cited by examiner

USE OF POLYPEPTIDES IN TREATING TISSUE INJURY

RELATED APPLICATION INFORMATION

This application claims the benefit of U.S. Provisional Application No. 60/802,082, filed May 19, 2006, the content of which application is specifically incorporated by reference herein in its entirety.

BACKGROUND

The basic living unit of the body is the cell, and each organ is an aggregate of many different cells held together by intercellular supporting structures. In the interstitial fluid (ISF) are the nutrients needed by the cells for maintenance of cellular life. One of the essential nutrients is protein (mainly albumin). Albumin binding water and electrolytes slow down entry of water and electrolytes into cell body, hence protecting the cells from swelling. Swelling may be thought of as the common pathway for all kinds of cellular damage, including hypoxia, ischemia, trauma, poisoning, infection etc.

Although the ISF derives from the blood, the concentration of protein in the ISF is always lower than that in the blood, about 7.3 gram/dl in plasma versus 2 to 3 gram/dl in the ISF. This is because that blood capillaries are only partially permeable to plasma protein. The ISF in central nervous system (CNS) contains the lowest concentration of protein (about 25 mg/dl), because of the blood brain barrier (BBB) and blood-cerebrospinal fluid barriers. As a result, cells in the bloodstream are more tolerant than cells in peripheral organ system, and cells in the peripheral organ system are much more tolerant than cells in the CNS.

In the capillaries of peripheral organ systems, adjacent endothelial cells form an intercellular cleft, which normally has a uniform spacing with a width of about 6 to 7 nanometers. The molecular weight of albumin is about 68,000 D, its diameter size is slightly larger than 7 nanometers. In addition, the endothelium and surrounding basement membrane are negatively charged, owing to the presence of exposed acidic residues. Proteins are amphoteric molecules carrying positive, negative, or neutral charges depending on the local pH environment. The net charge of a protein is the sum of all the negative and positive charges of its amino acid side chains, and its amino- and carboxyl-termini. The isoelectric point (pI) is the specific pH at which the net charge of the protein is zero. At a pH below the pI, proteins carry a net positive charge and vice-versa. Native albumin has a pI of about 4-4.8, and is therefore negatively charged at physiological pH. As a result, there is a rejective action between endothelium and albumin. Nevertheless, the ISF contains about 2-3 gram/dl of albumin in peripheral organ systems.

However, in the CNS, cerebral capillary endothelial cells are bound together with 'tight junctions', and the endothelium and basement membrane are strongly negatively charged. This forms the BBB and blood-cerebrospinal fluid barrier, which prevent albumin from entering the ISF and cerebrospinal fluid, and as a result, the ISF and the cerebrospinal fluid in the CNS only contain about 25 mg/dl of albumin.

In clinic, intravenous albumin injection has been used for treating various injuries. However, due to its large molecular weight and low pI, albumin does not easily enter the ISF to function. Substances of large molecular weight trend to increase fluid viscosity. High concentrations of albumin inside the blood stream lead to an increase of blood volume which may result in a heavy burden on the heart resulting in pulmonary edema. Therefore, intravenous albumin injection has had limited effect in protecting tissue.

SUMMARY

We have found that the concentration of protein in ISF mainly determines the tolerance to injuries, and that the higher the concentration of protein in the ISF, the more cellular tolerance to injuries. The limited passage of albumin, and of protein generally, into ISF, is due to large molecular weight and low isoelectric point (PI).

Accordingly, provided are methods and compositions for treating tissue injury that increase the concentration of protein in the ISF by use of polypeptide therapeutics designed to more easily cross the ISF. Specifically, provided is a method for treating tissue injury in a mammal, comprising administering a therapeutically effective amount of a polypeptide having an isoelectric point of at least about 4.8 and/or a molecular weight of less than about 30 kDa to the mammal.

Further, featured are kits for the shipping, storage or use of the compositions, as well the practice of the methods.

Other features and advantages of the invention will become apparent from the following detailed description and claims.

DETAILED DESCRIPTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "administering" includes any method of delivery of a compound of the present invention, including but not limited to, a pharmaceutical composition or therapeutic agent, into a subject's system or to a particular region in or on a subject. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "amino acid" is art-recognized and refers to all compounds, whether natural or synthetic, which include both an amino functionality and an acid functionality, including amino acid analogs and derivatives.

The terms "amino acid residue" and "peptide residue" are art-recognized and refer to an amino acid or peptide molecule without the —OH of its carboxyl group.

The term "amino acid residue" further includes analogs, derivatives and congeners of any specific amino acid referred to herein, as well as C-terminal or N-terminal protected amino acid derivatives (e.g. modified with an N-terminal or C-terminal protecting group).

The names of the natural amino acids are abbreviated herein in accordance with the recommendations of IUPAC-IUB.

The terms "comprise" and "comprising" are used in the inclusive, open sense, meaning that additional elements may be included.

The term "including" is used to mean "including but not limited to". "Including" and "including but not limited to" are used interchangeably.

The term "isolated polypeptide" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

The term "mammal" is known in the art, and exemplary mammals include humans, primates, bovines, porcines, canines, felines, and rodents (e.g., mice and rats).

A "patient," "subject" or "host" to be treated by the subject method may mean either a human or non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) other non-toxic compatible substances employed in pharmaceutical formulations; and (22) artificial cerebrospinal fluid.

The term "pharmaceutically-acceptable salts" is art-recognized and refers to the relatively non-toxic, inorganic and organic acid addition salts of compounds, including, for example, those contained in compositions of the present invention.

The "pI" of a polypeptide molecule is determined by the total sum of individual amino acids, and can be calculated using the pK values of amino acids.

The term "polypeptide" or "protein" as used herein refers to any amino acid polymer with peptide bond linkages.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "purified" refers to an object species that is the predominant species present (i.e., on a molar basis it is more abundant than any other individual species in the composition). Generally, a purified composition will have one species that comprises more than about 80 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a polypeptide of the invention using standard techniques for protein purification. Purity of a polypeptide may be determined by a number of methods known to those of skill in the art, including for example, amino-terminal amino acid sequence analysis, gel electrophoresis, mass-spectrometry analysis. etc.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "tissue injury" refers to any damage to the tissue of a subject, including, but not limited to hypoxia, ischemia, trauma, and poisoning.

The term "treating" is art-recognized and refers to curing as well as ameliorating at least one symptom of any condition or disease.

We have found that the passage of a polypeptide across a capillary into the ISF is determined by two factors, i.e. the molecular weight and the pI. Polypeptides with a smaller molecular weight pass through capillary walls more easily. Polypeptides with higher pI carry fewer negative charges, thus reducing rejective action between the endothelium and the polypeptides, easing their entry into ISF. Polypeptides with both lower molecular weight and higher pI exhibit a synergistic effect in ease of entering the ISF.

Accordingly, provided are methods and compositions for treating tissue injury that increase the concentration of protein in the ISF by use of polypeptide therapeutics designed to more easily enter the ISF. Specifically, provided is a method for treating tissue injury in a mammal, comprising administering a therapeutically effective amount of a polypeptide having an isoelectric point of at least about 4.8 and/or a molecular weight of less than about 30 kDa to the mammal.

Preferably, the polypeptides have a molecular weight between about 1 kDa to about 30 kDa. Polypeptides with pI higher than about 4.8 are preferred, with a pI between about 6 to about 8 is most preferred. The polypeptides should not easily enter cell body.

The specific amino acid sequence and structure of the polypeptides are not important, so long as the molecular weight and/or pI are in the effective range. Only non-toxic polypeptides are used. Preferably, the polypeptide has no specific biological function. However, polypeptides with a specific biological function may be used if they are denatured or do not cause serious complication if given in a large amount.

The preferred amino acid and percentage range of polypeptides useful in the methods are listed in the following Tables I and II:

TABLE I

Amino acid composition

| Amino acid | content (%) |
|---|---|
| Alanine | 0-20 |
| Arginine | 0-20 |
| Aspartic acid | 0-20 |
| Cystine | 0-30 |
| Cysteine | 0-30 |
| Glutamic acid | 0-30 |
| Glycine | 0-30 |
| Histine | 0-30 |
| Hydroxylysine | 0-30 |
| Hydroxyproline | 0-30 |
| Isoleucine | 0-30 |
| Leucine | 0-30 |
| Lysine | 0-20 |
| Methionine | 0-20 |
| Phenylalanine | 0-20 |
| Proline | 0-30 |
| Serine | 0-20 |
| Threonine | 0-20 |
| Tryptophan | 0-20 |
| Tyrosine | 0-20 |
| Valine | 0-20 |

TABLE II

Preferred amino acid range

| Amino acid | content (%) |
|---|---|
| Alanine | 4-10 |
| Arginine | 6-20 |
| Aspartic acid | 5-11 |
| Cystine | 0.1-6 |
| Cysteine | 0.1-0.7 |
| Glutamic acid | 10-17 |
| Glycine | 1.6-30 |
| Histine | 0.6-20 |
| Hydroxylysine | 0.6-1.8 |
| Hydroxyproline | 10-14 |
| Isoleucine | 1.5-2 |
| Leucine | 2-14 |
| Lysine | 3-25 |
| Methionine | 0.5-2 |
| Phenylalanine | 2-8 |
| Proline | 2-18 |
| Serine | 2-5 |
| Threonine | 1-4 |
| Tryptophan | 0-0.2 |
| Tyrosine | 0.4-6 |
| Valine | 2-3 |

The polypeptides may be isolated and purified from animal source. Gelatins deriving from animal skin, bone or other organ are good source of polypeptides for use in the methods, and various molecular weight ranges of gelatin are commercially available. Albumin may also be used in the methods. Sericin, consisting of proteins derived from silkworm cocoon, may also be used in the methods, and is commercially available.

Enzyme digestion, such as trypsin digestion, or hydrolysis by acid or base, may be used to produce polypeptides with molecular weights under 30 kDa.

A polypeptide is a "derivative" of another, as used herein, if it is a modification of a polypeptide, e.g., the product of processing a polypeptide with an enzyme, is a mutation of a particular polypeptide, a fragment of a particular polypeptide, etc.

The polypeptides can also be chemically synthesized or produced recombinantly, methods for which are well-known to those of skill in the art.

When polypeptides for use in the methods are chemically synthesized, a polymer with more amino acids having higher pI can be designed to yield polypeptides with higher pI. Alternatively, a hydrolytic process with acid can increase pI, for example, acid-cured gelatin (type A) has a higher pI between 7.0-9.0. Lime-cured gelatin (type B) has a lower pI, usually 4.7-5.2.

Of importance in designing a polypeptide for use in the methods is its water and electrolytes binding capacity. Polypeptides with larger molecular weight have more capacity to bind water and electrolytes. However, with more number of molecules, the polypeptides with smaller molecular weight can also reach same capacity. Theoretically, the polypeptides with larger molecular weight and smaller molecular weight are equally effective under same concentration (wt/dl) in the ISF. For example, 1% of polypeptide (1 gram per 100 ml) with molecular weight 10 kDa should be equally effective to 1% of polypeptide (1 gram per 100 ml) with molecular weight 20 kDa as they can bind similar amount of water and electrolytes.

To identify polypeptides that may be used in the methods, standard cell culture techniques, such as primary neuron culture, liver cell culture, muscle cell culture, etc., may be used to compare the efficacy with albumin. The optimal polypeptides may be selected by their ability to enter the ISF by measuring the polypeptides in the lymphatic system of an animal. The optimal polypeptides should be effective in standard cell culture system and have a higher concentration in the lymph of the organ system where protection is needed. If the polypeptides are intended to protect the CNS, the polypeptides should appear in the cerebrospinal fluid as well.

Design and preparation of the polypeptides may employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The polypeptides may be formulated into pharmaceutical compositions suitable for administration to a subject.

Such compositions may additionally comprise wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, saline, artificial cerebrospinal fluid, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Further provided are methods for treating and preventing tissue injury using the above polypeptide compositions.

Preferably the methods comprising delivering the polypeptides to the ISF to treat tissue injuries, e.g. by intravenous administration. The polypeptides intravenously administered can enter the ISF with ease, sustain cellular life in a similar manner as albumin and increase cellular tolerance to energy shortage. The treatment may be useful for both local damage affecting part of one organ, such as brain, heart, kidney, liver, muscle etc, and systemic damage affecting multi-organs or even the whole body, such as cardiac arrest and shock. The treatment is effective to fight against tissue injuries as long as cellular energy shortage or cellular edema occurs.

Alternatively, the polypeptides can be administered through the artery which supplies the local tissue where the protection is needed. The polypeptides used in this embodiment are less viscous as they have smaller molecular weight, and thus are less likely to develop pulmonary edema caused by blood volume increase as the polypeptides enter the ISF quickly.

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 5 g per kg, and more specifically in the range of about 0.1 g to about 1 g per kg. Preferably the dosage is determined such that maximum concentration measured in the ISF-lymph system of the subject is without limit, however, it is preferred to be under 16 g/dl.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$ or limit test. Acute toxicity can be assessed using increasing doses in mice and rodents. Exploratory acute toxicity in mice and/or rats after single dose may be undertaken to begin estimation of the therapeutic window of inhibitors and to identify the potential target organs of toxicity. As candidate selection nears, these studies may provide guidance for the selection of proper doses in multi-dose studies, as well as establish any species specific differences in toxicities. These studies may be combined with routine PK measurements to assure proper dosages were achieved. Generally 3-4 doses will be chosen that are estimated to span a range having no effect through to higher doses that cause major toxic, but non-lethal, effects. Animals will be observed for effects on body weight, behavior and food consumption, and after euthanasia, hematology, blood chemistry, urinalysis, organ weight, gross pathology and histopathology will be undertaken.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

The efficacy of treatment with the subject compositions may be determined in a number of fashions known to those of skill in the art.

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

EXEMPLIFICATION

The invention now being generally described, it will be more readily understood by reference to the following examples which are included merely for purposes of illustration of certain aspects and embodiments of the present invention, and are not intended to limit the invention in any way.

Example 1

Method of Identifying Useful Polypeptides for Treating Tissue Injury

Neuron culture: Cortical neurons cultures were prepared from fetal Sprague-Dawley rats at 17-day gestation. Timed pregnant Sprague-Dawley rats were euthanized with isoflorane. After dissection of the cortical region of the fetal brain, cortical neurons were dispersed by trituration, centrifuged at 250 g for 5 minutes at 4° C., and suspended in a neurobasal medium supplemented with 25 μmol/L glutamic acid, 0.5 mmol/L glutamine, 1% antibiotic-antimycotic solution, and 2% B27 supplement. Cells were plated at $5 \times 10^5$ cells/ml on poly-L-lysine-coated 24-well plates. Cytosine (10 μmol/) was added at day 3. Neuron cultures were fed every 4 days with replacement of half of neurobasal medium containing 0.5 mmol/L glutamine, 1% antibiotic-antimycotic solution, and 2% B27 supplement. The culture plates were incubated at 37° C. in a humid atmosphere with 5% $CO_2$.

In vitro neuron viability experiments were performed on cultures at 10-12 days. Specifically, cell culture media were replaced respectively by the following solutions:

A. Artificial cerebrospinal fluid (ACSF): $Na^+$ 150 mEq/L, $K^+$ 3.0 mEq/L, $Mg^{2+}$ 0.8 mEq/L, $Ca^{2+}$ 1.4 mEq/L, P 1.0 mEq/L, $Cl^-$ 155 mEq/L, pH 7.0.

B. 2 wt % albumin (molecular weight 68 kDa, pI 4.8)+ACSF

C. 2 wt % polypeptides from trypsin digested albumin (molecular weight 5-30 kDa, pI 4.6-4.8)+ACSF D. 2 wt % polypeptide from trypsin digested albumin which is further processed for increasing the pI by carbodiimide and ethylene diamine (molecular weight 5-30 kDa, pI 7)+ACSF E. 2 wt % polypeptide from porcine skin gelatin digested by hydrochloride acid (molecular weight 1-10 kDa, pI 7-9)+ACSF F. 2 wt % β-Lactoglobulin (molecular weight 18 kDa, pI 5.3)+ACSF Anoxic insult: After the above treatment, all cultures were subjected to an anaerobic environment of 95% $N_2$, 5% $CO_2$ for 60 minutes at 37° C. in a chamber. Anoxia was terminated by replacement of a normal culture medium and by returning the cultures to a standard incubator maintained at 37° C. in 5% $CO_2$.

Validation of neurons' survival: Neuronal viability was quantitatively evaluated by a methyl thiazole tetrazolium (MTT) reduction test. This quantifies the formation of a dark blue formazan product formed by the reduction of the tetrazolium ring of MTT by the mitochondrial succinate dehydrogenase in living cells. Specifically, twenty-four hours after anoxia, the cultures were incubated with MTT (250 μg/ml) at 37° C. in a culture medium for 3 hours. The cultures were then washed and incubated in 0.08 N HCl/isopropanol to dissolve the blue formazan product. Cell viability corresponded to the value of the optical density read at 570 nm with background subtraction at 630 nm. Results were expressed as percent of the optical density measured in normal control cells.

Results:

| Treatment | anoxia | Neuron's viability (Percentage, Mean ± SD) |
| --- | --- | --- |
| Culture medium | 0 mins | 100 ± 4.5 |
| A | 60 mins | 44 ± 5.5 |
| B | 60 mins | 96 ± 3.9 |
| C | 60 mins | 93 ± 5.8 |
| D | 60 mins | 94 ± 4.8 |
| E | 60 mins | 97 ± 5.8 |
| F | 60 mins | 95 ± 3.2 |

When the neuronal cell culture medium was replaced by the ACSF and exposed to an anoxic environment, there was a low viability of neurons (A). Supplementing ACSF with native bovine serum albumin significantly increased neuronal viability (B). Supplementing ACSF with polypeptides of low molecular weight with various pI value also significantly increased neuron's viability (C-F).

These results suggest albumin as an extracellular protein is important to fight against cell injuries, such as hypoxia-ischemia, and the polypeptides of low molecular weight with various pI value can replace albumin. These results also suggest that primary cell culture is good method to identify useful polypeptides in this application.

Example Two

Ability of the Polypeptides to Enter the ISF

12 Sprague-Dawley rats weighting between 180-200 grams were divided in two groups. Group one (n=6): albumin treatment (molecular weight 68 kDa, pI 4.8). Group two (n=6): the polypeptide treatment (from porcine skin gelatin digested by hydrochloride acid, molecular weight 1-10 kDa, pI 7-9).

Rats were anesthetized with Ketamine/xylazine 30 mg/kg ip. To collect the CSF, a small cannula was implanted into the cistern magna in each rat according to a method of Barth (A simple and reliable technique to monitor intracranial pressure in the rat: Technical note. *Neurosurgery*. 1992 30: 138-140). To collect lymph, incision was made in the lower abdomen to expose the lower part of the abdominal thoracic duct, and the lymph vessel draining left leg was cannulated with a tiny plastic tubing which was filled with undiluted heparin.

In group one, 10 μl of the CSF was collected, and the CSF was drained away as completely as possible. Then, 2.5 gram/kg of albumin was administered iv in 20 minutes. Two hours after completion of injection, 10 μl of the CSF was collected again.

In group two, 10 μl of the lymph were also collected. Then, 2.5 gram/kg of the polypeptides was administered iv in 20 minutes. 20 minutes after completion of injection, 10 μl of the lymph was collected again.

The total protein concentrations of the CSF and the lymph from left leg were measured by a standard method (Lowry et al. Protein measurement with the Foin phenol reagent. *J. Biol. Chem.* 1951. 193:265-275)

Results:

| Treatment | CSF protein concn (mg/dl) | | Lymph protein concn | |
|---|---|---|---|---|
| | Before | After | Before | After |
| Group one (n = 6) | 25 ± 3.4 | 28 ± 6.7 | 2.2 ± 0.3 | 2.8 ± 0.4 |
| Group two (n = 6) | 24 ± 4.5 | 140 ± 9.6 | 2.1 ± 0.2 | 5.1 ± 0.3 |

These results suggest that intravenous injection of high dose albumin (molecular weight 68 kDa, pI 4.8) did not enter significantly into the CSF which is the continuation of ISF in the CNS, and the injected albumin mainly stays inside the blood vessel, as it only shows a slight increase of protein concentration in the lymph. However, the polypeptides (molecular weight 1-10 kDa, pI 7-9) not only passes through the capillary wall entering the ISF more easily in the peripheral organ system, but also crosses the BBB and Blood-CSF barrier, entering the CSF in the CNS.

Example Three

Treatment for Brain Ischemia

12 Sprague-Dawley rats weighing between 180-200 grams were divided in two groups. Group one (n=6): treatment with saline. Group two (n=6): treatment with the polypeptide (from porcine skin gelatin digested by hydrochloride acid, molecular weight 1-10 kDa, pI 7-9).

Induction of cerebral ischemia: Ketamine/xylazine 30 mg/kg ip was given for anesthesia. A midline incision on the neck was made. The left common carotid artery, the external carotid artery (ECA) and the internal carotid artery (ICA) were exposed. The ECA was ligated and severed. Focal cerebral ischemia was produced by advancing a 3.0 nylon suture from the ECA to ICA to block the origin of left middle cerebral artery. The nylon suture was left in place to induce focal cerebral ischemia on left hemisphere supplied by middle cerebral artery. The ischemia was lasted for 3 hours, the nylon suture was then removed to allow blood reperfusion for 21 hours.

Treatment: The treatment was given at 3 hours of ischemia. In group one, 2 ml of saline was administered intravenously. The infusion lasted for 2 hours at rate of 1 ml/hour. In group two, 2.5 gram/kg of the polypeptides (molecular weight 1-10 kDa, pI 7-9) was administered intravenously. The infusion lasted for 2 hours at rate of 1 ml/hour.

Neurological deficit test: At 24 hours after the induction of cerebral ischemia, each of the subject rats was evaluated for evidence of behavioral deficits. A score of 0-4 was used to assess the motor and behavioral changes. Score 0: No apparent deficits, Score 1: Contralateral forelimb flexion, Score 2: Decreased grip of the contralateral forelimb when the tail is pulled, Score 3: Spontaneous movement in all directions; contralateral circling only if pulled by tail and Score 4: Spontaneous contralateral circling.

Infarct volume evaluation: After the behavioral testing, all rats were euthanized and the brains were harvested. Sections of 1 mm in thickness were cut and stained with 2% 2,3,5-triphenyltetrazolium chloride (TTC) in phosphate buffer at 37° C. for 10 minutes and then fixed in 10% formalin. Viable tissue and necrotic tissue were distinguished by TTC staining and the infarct volumes were calculated and analyzed with computer software and expressed as the percentage of the whole brain volume.

Results: In group one, the average neurological deficit score was 3.25±0.7, and the average infarct volume was 25±1.79%. In group two, the average neurological deficit score was 1.2±0.7, and the average infarct volume was 8.26±1.39%. It was thus concluded that the polypeptides with lower molecular weight and higher pI significantly reduce the infarct volume and ameliorate the behavioral deficits.

Example Four

Treatment for Hemorrhagic Shock

12 Sprague-Dawley rats weighing between 180-200 gram were divided in two groups. Group one (n=6): treatment with 10% Dextran. Group two (n=6): treatment with the polypeptide (from porcine skin gelatin digested by hydrochloride acid, molecular weight 1-10 kDa, pI 7-9).

Ketamine/xylazine 30 mg/kg ip was given for anesthesia. The right femoral artery was cannulated with a catheter for measurement of mean arterial pressure (MAP) during the experiment. The right femoral vein was cannulated with a catheter to withdraw blood.

Following surgical cannulations above, all rats were allowed to stabilize for 30 minutes. Bleeding was carried out in 2 phases. Initially, 21 mL/kg of blood was withdrawn over 20 minutes. Immediately thereafter, an additional 12.5 mL/kg of blood was withdrawn over 40 minutes. Thus, hemorrhage occurred over a total period of 60 minutes and the total blood loss was 33.5 mL/kg or approximately 55% of total blood volume. In group one, 5 ml of 10% Dextran was administered intravenously over period of 30 minutes. In group two, 5 ml of the polypeptides (molecular weight 1-10 kDa, pI 7-9) was administered intravenously over period of 30 minutes, and total of 2.5 gram/kg of the polypeptides were administered for each rat. All rats were observed for 6 hours or until expiration (defined by apnea for >1 minute).

Results: After lethal massive blood loss, hemorrhagic shock occurred in all animals. In group one (10% Dextran treated), 4 rats died within 2 hours after the end of the bleeding protocol and all died within 3 hours. In group two (the polypeptide treated), 1 rats died at 4 hours, 5 rats survived for the whole 6 hours postbleeding observation period.

REFERENCES

All publications and patents mentioned herein, including those listed below, are hereby incorporated by reference in their entirety as if each individual publication or patent was specifically and individually incorporated by reference. In case of conflict, the present application, including any definitions herein, will control.

Guyton A C. Hall J E. *Textbook of Medical Physiology*, ninth edition, Chapter 16, page 183-197. WB Saunders company.

Guyton A C. Hall J E. *Textbook of Medical Physiology*, ninth edition, Chapter 25, page 297-313. WB Saunders company.

Ames A, Wright R L, Kowada M, Thurston J M, Majno G. Cerebral ischemia: II. The no-reflow phenomenon. *Am. J. Pathol*. 1968; 52(2):437-53.

Kloner R A. Foreword-No-reflow: Basic science to a clinical phenomenon. *Basic Res Cardiol*. 2006. 101:357-358.

Fischer M, Hossmann K A. No-reflow after cardiac arrest. *Intensive Care Med*. 1995; 21(2):132-41.

Bottiger B W, Krumnikl J J, Gass P, Schmitz B, Motsch J, Martin E. The cerebral "no-reflow" phenomenon after cardiac arrest in rats. Influence of low-flow reperfusion. *Resuscitation*. 1997; 34(1):79-87.

Follis F, Miller K, Seremin O U, Pett S, Kessler R, Temes T, Wernly J A. Experimental delayed postischemic spinal cord hypoperfusion after aortic cross-clamping. *Can. J. Neurol Sci*. 22 (1995) 202-207.

Milhorat T H, Hammock M K, Fenstermacher J D, Levin V A: Cerebrospinal fluid production by the choroids plexus and brain. *Science* 1971, 173:330-332.

Milhorat T H: choroids plexus and cerebrospinal fluid production. *Science* 1969, 166:1514-1516.

Rosenberg G A, Kyner W T, Estrada E. Bulk flow of brain interstitial fluid under normal and hyperosmolar conditions. *Am J Physiol*. 1980. 238:F42-49

Abbott N J. Evidence for bulk flow of brain interstitial fluid: significance for physiology and pathology. *Neurochemistry International*. 2004; 45:545-5452.

Watkins S, Madison J, Galliano M, Minchiotti L, Putnam F W. Analbuminemia: three cases resulting from different point mutations in the albumin gene. *Proc. Natl. Acad. Sci. USA*. 1994. 91:9417-9421.

Ruffner D E. Dugaiczyk A. Splicing mutation in human hereditary analbuminemia. *Proc. Natl. Acad. Sci. USA*. 1988. 85:2125-2129.

Nagase S. Shimamune K. Albumin-deficient rat mutant. *Science*. 1979. 205:590-591.

Hua L. et al. Elevation of serum albumin levels in nagase analbuminemic rats by allogeneic bone marrow cell transplantation. *Eur. Surg. Res*. 2005. 37:111-114.

Fluid physiology. 7.3 Colloids. http://www.anaesthesiamcq.com/FluidBook/fl7_3.php Rainey T S, Read C A. The pharmacologic approach to the critically ill patient. 3rd Baltimore: Williams and Wilkins. 1994. Chapter 15. 272-290.

Zinderman C E, Landow L, Wise R P. Anaphylactoid reactions to Dextran 40 and 70: reports to the United States Food and Drug Administration, 1969 to 2004. *J. Vasc. Surg*. 2006 43:1004-1009.

Fishman R A. Exchange of albumin between plasma and cerebrospinal fluid. *Am. J. Physiol*. 1953. 175:96-98.

Griffin D E, Giffels J. Study of protein characteristics that influence entry into the cerebrospinal fluid of normal mice and mice with encephalitis. *J. Clin. Invest*. 1982. 70:289-295.

Kumagai A K, Eisenberg J B, Paradridge W M. Absorptive mediated endocytosis of cationized albumin and β-endorphin-cationized albumin chimeric peptide by isolated brain capillaries. *J. Biol. Chem*. 1987. 262:15214-15219.

Lu W, Zhang Y, Tan Y Z, Hu K L, Jiang X G, Fu S K. Cationic albumin-conjugated pegylated monoparticles as novel drug carrier for brain delivery. *Journal of controlled release*. 2005. 107:428-448.

Pardridge W M, Kumagai A K, Eisenberg J B. Chimeric peptides as a vehicle for peptide pharmaceutical delivery through the blood-brain barrier. *Biochem Biophys Res Commun*. 1987 Jul. 15; 146(1):307-13.

Pardridge W M, Triguero D, Buciak J L. β-Endorphin chimeric peptides: Transport through the Blood-brain barrier in vivo and cleavage of disulfide linkage by brain. *Endocrinology*. 1990/126:977-984.

Pardridge W M, Triguero D, Nuciak J, Yang J. Evaluation of cationized rat albumin as potential blood-brain barrier drug transport vector. *The Journal of pharmacology and experimental therapeutics*. 1990. 255: 893-899.

Pardridge W M, Boado R J, Black K L, Cancilla P A. Blood-brain barrier and new approaches to brain drug delivery. *West J Med*. 1992. 156:281-286.

Sakane T, Pardridge W M. Carboxyl-directed pegylation of brain-derived neurotrophic factor markedly reduces systemic clearance with minimal loss of biologic activity. *Pharmaceutical Research*. 1997. 14:1085-1091.

Wu D, Pardridge W M. Neuroprotection with noninvasive neurotrophin delivery to the brain. *Proc. Natl. Acad. Sci. USA*. 1999. 96:254-259.

Zhang Y, Pardridge W M. Conjugation of brain-derived neurotrophic factor to a blood-brain barrier drug targeting system enables neuroprotection in regional brain ischemia following intravenous injection of the neurotrophin. *Brain Research*. 2001. 889:49-56.

Zhang Y, Pardridge W M. Neuroprotection in transient focal brain ischemia after delayed intravenous administration of brain-derived neurotrophic factor conjugated to a blood-brain barrier drug targeting system. *Stroke*. 2001. 32:1378-1384.

Pardridge W M. Targeting neurotherapeutic agents through the blood-brain barrier. *Arch. Neurol.* 2002. 59:35-40.

Pardridge W M. Blood-brain barrier drug targeting: the future of brain drug development. *Molecular Interventions.* 2003. 3:90-105.

Song B W, Vinters H V, Wu D, Pardridge W M. Enhanced neuroprotective effects of basic fibroblast growth factor in regional brain ischemia after conjugation to a blood brain barrier delivery vector. *J. Pharmacol. Exp. Ther.* 2002. 301:605-610.

Pardridge W M. The blood brain barrier: Bottleneck in brain drug development. *NeuroRx.* 2005. 1:3-14.

Pardridge W M. Editorial. The blood brain barrier and neurotherapeutics. *NeuroRx.* 2005. 1:1-2.

Pardridge W M, Kang Y S, Diagne A, Zack J A. Cationized hyperimmune immunoglobulins: pharmacokinetics, toxicity evaluation and treatment of human immunodeficiency virus-infected human-peripheral blood lymphocytes-severe combined immune deficiency mice. *J. Pharmacol. Exp. Ther.* 1996 January; 276(1):246-252.

Shimon-Hophy M. Wadhwani K C. Chandrasekaran K, Larson D., Smith Q R. Rapoport S I. Regional blood-brain barrier transport of cationized bovine serum albumin in awake rats. *Am. J. Physiol.* 1991. 261:R478-483.

Wadhwani K C. Shimon-Hophy M. Rapoport S I. Enhanced permeabilities of cationized-bovine serum albumins at the blood nerve and blood-brain barrier in awake rats. *J. Neurosci. Res.* 1992. 32:407-414.

Pardridge W M. Neuroprotection in stroke: is it time to consider large-molecule drugs? *Drug Discov. Today.* 2001. 6:751-753.

Pardridge W M. Molecular Trojan horses for blood-brain barrier drug delivery. *Curr. Opin. Pharmacol.* 2006 October; 6(5):494-500

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

The invention claimed is:

1. A method for treating tissue injury in a mammal in need of such a treatment, comprising administering a therapeutically effective amount of a polypeptide having an isoelectric point of higher than 4.8 and a molecular weight of less than 30 kpa to the mammal,
   wherein the polypeptide is a digested albumin that has been treated with trypsin, wherein the amount of polypeptide is effective to sustain cellular life, and wherein the tissue injury is brain tissue injury or hemorrhagic shock.

2. A method for treating tissue injury in a mammal in need of such a treatment, comprising administering a therapeutically effective amount of a gelatin having an isoelectric point of 7-9 and a molecular weight of 1-10 kpa to the mammal,
   wherein the amount of the gelatin is effective to sustain cellular life, and wherein the tissue injury is brain tissue injury or hemorrhagic shock.

\* \* \* \* \*